(12) United States Patent
Shi et al.

(10) Patent No.: US 8,791,239 B2
(45) Date of Patent: Jul. 29, 2014

(54) FIBROUS ASSEMBLIES FOR ANTIBODY PRESENTATION, AND MULTIPLEXED ANTIGENIC ANALYSIS USING SAME

(75) Inventors: Xiao-Wen Shi, College Park, MD (US); Hsuan-Chen Wu, Greenbelt, MD (US); Gregory F. Payne, Hunt Valley, MD (US); William E. Bentley, St. Michaels, MD (US)

(73) Assignee: University of Maryland, College Park, College Park, MD (US)

( * ) Notice: Subject to any disclaimer, the term of this patent is extended or adjusted under 35 U.S.C. 154(b) by 609 days.

(21) Appl. No.: 12/990,981

(22) PCT Filed: Apr. 7, 2009

(86) PCT No.: PCT/US2009/039799
§ 371 (c)(1),
(2), (4) Date: Apr. 25, 2011

(87) PCT Pub. No.: WO2009/137211
PCT Pub. Date: Nov. 22, 2009

(65) Prior Publication Data
US 2011/0195860 A1    Aug. 11, 2011

Related U.S. Application Data

(60) Provisional application No. 61/050,252, filed on May 4, 2008.

(51) Int. Cl.
A61K 38/00 (2006.01)
A61K 9/51 (2006.01)
C08L 5/08 (2006.01)

(52) U.S. Cl.
CPC *A61K 9/5169* (2013.01); *C08L 5/08* (2013.01)
USPC ........................................................ 530/350

(58) Field of Classification Search
CPC ................................ C08L 5/08; A61K 9/5169
See application file for complete search history.

(56) References Cited

U.S. PATENT DOCUMENTS

| | | | |
|---|---|---|---|
| 2002/0081280 A1* | 6/2002 | Curiel et al. | 424/93.2 |
| 2006/0102486 A1 | 5/2006 | Bentley et al. | |
| 2006/0292680 A1* | 12/2006 | Barbari et al. | 435/178 |
| 2007/0068824 A1 | 3/2007 | Payne et al. | |

FOREIGN PATENT DOCUMENTS

WO    02102432 A1    12/2002

OTHER PUBLICATIONS

Nalbantoglu et al., American Journal of Pathology, May 1994, vol. 144, No. 5, 874.*
Charcosset et al., Biotechnology and Bioengineering, 1995, vol. 48, pp. 415-427.*
Shi et al., Biomacromolecules 2008, 9, 1417-1423.*
Kang, X., et al., "A novel glucose biosensor based on immobilization of glucose oxidase in chitosan on a glassy carbon electrode modified with gold-platinum alloy nanoparticles/multiwall carbon nanotubes", "Analytical Biochemistry", Jul. 7, 2007, pp. 71-79, vol. 369.
Luo, X., et al, "A glucose biosensor based on chitosan-glucose oxidase-gold nanoparticles biocomposite formed by one-step electrodeposition", "Analytical Biochemistry", Aug. 24, 2004, pp. 284-289, vol. 334.
Ahmed, S., et al., "Controlling the orientation of immobilized proteins on an affinity membrane through chelation of a histidine tag to a chitosan-Ni++ surface", "Journal of Membrane Science", Mar. 6, 2006, pp. 553-559, vol. 280.
Akerstroem, B., et al., "Protein G: A Powerful Tool for Binding and Detection of Monoclonal and Polyclonal Antibodies", "Journal of Immunology", Oct. 1985, pp. 2589-2592, vol. 135, No. 4.
Akerstroem, B., et al., "A Physicochemical Study of Protein G, a Molecule with Unique Immunoglobulin G-binding Properties", "Journal of Biological Chemistry", Aug. 5, 1986, pp. 10240-10247, vol. 261, No. 22.
Bang, E., et al., "Durable Antimicrobial Finish of Cotton Fabrics", "Journal of Applied Polymer Science", Jul. 3, 2007, pp. 938-943, vol. 106.
Blankespoor, R., et al., "Dense Monolayers of Metal-Chelating Ligands Covalently Attached to Carbon Electrodes Electrochemically and Their Useful Application in Affinity Binding of Histidine-Tagged Proteins", "Langmuir", Mar. 12, 2005, pp. 3362-3375, vol. 21.
Cha, H., et al., "Observations of Green Fluorescent Protein as a Fusion Partner in Genetically Engineered Escherichia coli: Monitoring Protein Expression and Solubility", "Biotechnology and Bioengineering", Mar. 5, 2000, pp. 565-574, vol. 67, No. 5.
Cresce, A., et al., "Nanopatterning of Recombinant Proteins Using Block Copolymer Templates", "Macromolecules", Jul. 26, 2006, pp. 5826-5829, vol. 39.
Ding, B., et al., "Formation of novel 2D polymer nanowebs via electrospinning", "Nanotechnology", Jun. 27, 2006, pp. 3685-3691, vol. 17.
Duran, N., et al., "Antibacterial Effect of Silver Nanoparticles Produced by Fungal Process on Textile Fabrics and Their Effluent Treatment", "Journal of Biomedical Nanotechnology", Jun. 2007, pp. 203-208, vol. 3, No. 2.

(Continued)

*Primary Examiner* — Marcela M Cordero Garcia
*Assistant Examiner* — Kaipeen Yang
(74) *Attorney, Agent, or Firm* — Hulquist, PLLC; Steven J. Hulquist; Mary B. Grant (57) ABSTRACT

Biofunctionalized fibers including a fiber platform and a histidine-tagged protein and, optionally, an antibody. Chitosan is a fiber useful as the fiber platform. The fiber platform may be treated with nickel or may be directly linked to the histidine-tagged protein e.g., histidine-tagged streptococcal IgG-binding protein, protein G, protein G3T, GFP or RFP. The resulting biofunctionalized fibers can be assembled into protein fiber assemblies by a variety of biofabrication methods. The fiber assemblies, e.g., in the form of woven fabrics, are useful for (i) antigen capture; (ii) immunoanalysis; and/or (iii) multiplexed analysis. In one fabrication, each fiber of a fiber assembly presents a specific antibody, and mixing and matching of fibers, for example by weaving of fabrics from various antibody-presenting fibers, allows for multiple antigens to be captured simultaneously for multiplexed analysis.

19 Claims, 8 Drawing Sheets

(56) References Cited

OTHER PUBLICATIONS

El-Tahlawy, K., et al., "Chitosan: Aspects of Fiber Spinnability", "Journal of Applied Polymer Science", Jan. 30, 2006, pp. 1162-1168, vol. 100.

Gamage, A., et al., "Use of chitosan for the removal of metal ion contaminants and proteins from water", "Food Chemistry", Jun. 8, 2007, pp. 989-996, vol. 104.

Gao, D., et al., "Fabrication of Antibody Arrays Using Thermally Responsive Elastin Fusion Proteins", "J. Am. Chem. Soc.", Dec. 27, 2005, pp. 676-677, vol. 128.

Guibal, E., "Interactions of metal ions with chitosan-based sorbents: a review", "Separation and Purification Technology", Jul. 15, 2004, pp. 43-74, vol. 38.

Hegemann, D., "Stain Repellent Finishing on Fabrics", "Advanced Engineering Materials", May 2005, pp. 401-404, vol. 7, No. 5.

Jain, P., et al., "High-Capacity Purification of His-tagged Proteins by Affinity Membranes Containing Functionalized Polymer Brushes", "Biomacromolecules", Sep. 19, 2007, pp. 3102-3107, vol. 8.

Ji, F., et al., "Smart polymer fibers with shape memory effect", "Smart Mater. Struct.", Sep. 25, 2006, pp. 1547-1554, vol. 15.

Kim, S., et al., "Dual-Mode Fluorophore-Doped Nickel Nitrilotriacetic Acid-Modified Silica Nanoparticles Combine Histidine-Tagged Protein Purification with Site-Specific Fluorophore Labeling", "J. Am. Chem. Soc.", Oct. 2, 2007, pp. 13254-13264, vol. 129.

Kumbar, S., et al., "Polymeric Nanofibers as Novel Carriers for the Delivery of Therapeutic Molecules", "Journal of Nanoscience and Nanotechnology", Sep.-Oct. 2006, pp. 2591-2607, vol. 6.

Lata, S., et al, "Stable and Functional Immobilization of Histidine-Tagged Proteins via Multivalent Chelator Headgroups on a Molecular Poly(ethylene glycol) Brush", "Analytical Chemistry", Jan. 11, 2005, pp. 1096-1105, vol. 77.

Lee, J., et al., "Direct Immobilization of Protein G Variants with Various Numbers of Cysteine Residues on a Gold Surface", "Analytical Chemistry", Mar. 7, 2007, pp. 2680-2687, vol. 79.

Lim, S., et al., "Review of Chitosan and Its Derivatives as Antimicrobial Agents and Their Uses as Textile Chemicals", "Journal of Macromolecular Science Part C—Polymer Reviews", 2003, pp. 223-269, vol. C43, No. 2.

Marculescu, D., et al., "Electronic Textiles: A Platform for Pervasive Computing", "Proceedings of the IEEE", Dec. 2003, pp. 1995-2018, vol. 91, No. 12.

Nair, L., et al., "Development of novel tissue engineering scaffolds via electrospinning", "Expert Opin. Biol. Ther.", May 2004, pp. 659-668, vol. 4, No. 5.

Paborsky, L., et al., "A Nickel Chelate Microtiter Plate Assay for Six Histidine-Containing Proteins", "Analytical Biochemistry", Feb. 1, 1996, pp. 60-65, Article No. 0050, vol. 234.

Pavlov, M., et al., "Fibers and 3D Mesh Scaffolds from Biodegradable Starch-Based Blends: Production and Characterization", "Macromolecular Bioscience", Aug. 9, 2004, pp. 776-784, vol. 4.

Pavon-Djavid, G., et al., "Bioactive Poly(ethylene terephthalate) Fibers and Fabrics: Grafting, Chemical Characterization, and Biological Assessment", "Biomacromolecules", Oct. 11, 2007, pp. 3317-3325, vol. 8.

Payne, G., et al., "Chitosan: a soft interconnect for hierarchical assembly of nano-scale components", "Soft Matter", Jan. 16, 2007, pp. 521-527, vol. 3.

Qin, Y., et al., "Absorption and Release of Zinc and Copper Ions by Chitosan Fibers", "Journal of Applied Polymer Science", Mar. 27, 2007, pp. 527-532, vol. 105.

Rhazi, M., et al., "Influence of the nature of the metal ions on the complexation with chitosan. Application to the treatment of liquid waste", "European Polymer Journal", Aug. 2002, pp. 1523-1530, vol. 38.

Rinaudo, M., "Chitin and chitosan: Properties and applications", "Progress in Polymer Science", Jul. 2006, pp. 603-632, vol. 31.

Rusmini, F., et al., "Protein Immobilization Strategies for Protein Biochips", "Biomacromolecules", Apr. 20, 2007, pp. 1775-1789, vol. 8.

Schauer, C., et al., "Color changes in chitosan and poly(allyl amine) films upon metal binding", "Thin Solid Films", Jun. 23, 2003, pp. 250-257, vol. 434.

Schiffman, J., et al, "Cross-Linking Chitosan Nanofibers", "Biomacromolecules", Dec. 30, 2006, pp. 594-601, vol. 8.

Schiffman, J., et al, "One-Step Electrospinning of Cross-Linked Chitosan Fibers", "Biomacromolecules", Aug. 14, 2007, pp. 2665-2667, vol. 8.

Shi, Q., et al., "Chitosan-coated silica beads as immobilized metal affinity support for protein adsorption", "Biochemical Engineering Journal", Dec. 2003, pp. 317-322, vol. 16, No. 3.

Steinbacher, J., et al., "Polymer Chemistry in Flow: New Polymers, Beads, Capsules, and Fibers", "Journal of Polymer Science: Part A: Polymer Chemistry", Oct. 11, 2006, pp. 6505-6533, vol. 44.

Tanaka, G., et al., "Fabrication of an antibody microwell array with self-adhering antibody binding protein", "Analytical Biochemistry", Jan. 17, 2006, pp. 298-303, vol. 350.

Tinazli, A., et al., "Native protein nanolithography that can write, read and erase", "Nature Nanotechnology", Mar. 18, 2007, pp. 220-225, vol. 2.

Vijayendran, R., et al., "A Quantitative Assessment of Heterogeneity for Surface-Immobilized Proteins", "Analytical Chemistry", Dec. 23, 2000, pp. 471-480, vol. 73, No. 3.

Wei, Y., et al., "The Crosslinking of Chitosan Fibers", "Journal of Polymer Science: Part A: Polymer Chemistry", 1992, pp. 2187-2193, vol. 30.

Woolfson, D., et al., "Peptide-based fibrous biomaterials: some things old, new and borrowed", "Current Opinion in Chemical Biology", Oct. 9, 2006, pp. 559-567, vol. 10.

Xi, F., et al., "Macroporous chitosan layer coated on non-porous silica gel as a support for metal chelate affinity chromatographic adsorbent", "Journal of Chromatography A", Nov. 19, 2004, pp. 41-47, vol. 1057.

Xu, L, et al., "Polyoxometalate-Modified Fabrics: New Catalytic Materials for Low-Temperature Aerobic Oxidation", "Journal of Catalysis", Oct. 2000, pp. 394-405, vol. 195.

Yi, H., et al, "Biofabrication with Chitosan", "Biomacromolecules", Sep. 3, 2005, pp. 2881-2894, vol. 6, No. 6.

Zhen, G., et al., "Nitrilotriacetic Acid Functionalized Graft Copolymers: A Polymeric Interface for Selective and Reversible Binding of of Histidine-Tagged Proteins", "Advanced Functional Materials", Sep. 29, 2005, pp. 243-251, vol. 16.

Shi, X., et al., "Chitosan Fibers: Versatile Platform for Nickel-Mediated Protein Assembly", "Biomacromolecules", Apr. 10, 2008, pp. 1417-1423, vol. 9.

Ho, M., et al, "Preparation and characterization of RGD-immobilized chitosan scaffolds", "Biomaterials", Oct. 14, 2004, pp. 3197-3206, vol. 26.

Shi, X., et al., "Chitosan Biotinylation and Electrodeposition for Selective Protein Assembly", "Macromolecular Bioscience", May 13, 2008, pp. 451-457, vol. 8.

\* cited by examiner

1: chitosan fiber + GFP (negative control)
2: chitosan fiber + (protein G3T + tyrosinase) + anti-BSA + GFP (experimental)
3: chitosan fiber + (protein G3T + tyrosinase) + anti-GFP + GFP (positive control)
4: chitosan fiber + BSA(Texas red labeled) (negative control)
5: chitosan fiber + (protein G3T + tyrosinase) + anti-GFP + BSA (experimental)
6: chitosan fiber + (protein G3T + tyrosinase) + anti-BSA + BSA (positive control)

FIBROUS ASSEMBLIES FOR ANTIBODY PRESENTATION, AND MULTIPLEXED ANTIGENIC ANALYSIS USING SAME

CROSS-REFERENCE TO RELATED APPLICATIONS

This application is a U.S. national phase application under the provisions of 35 U.S.C. §371 of International Patent Application No. PCT/US09/39799 filed Apr. 7, 2009, which in turn claims priority of U.S. Provisional Patent Application No. 61/050,252 filed May 4, 2008. The disclosures of such international patent application and U.S. priority patent application are hereby incorporated herein by reference in their respective entireties, for all purposes.

GOVERNMENTAL RIGHTS IN INVENTION

This invention was made with governmental support under Grant Nos. CBET-0650650 and EFRI-0735987, awarded by the Chemical, Bioengineering, Environmental, and Transport Systems (CBET) and Emerging Frontiers in Research and Innovation (EFRI) divisions of the National Science Foundation (NSF) and under Grant No. 60NANB6D6169 awarded by the National Institute of Standards and Technology (NIST). The government has certain rights in the invention.

Funding has also been provided by the R.W. Deutsch Foundation.

FIELD OF THE INVENTION

The invention relates generally to biofunctionalized fibers and to protein fiber assemblies made up of such biofunctionalized fibers. More specifically the invention relates to chitosan-containing fibers biofunctionalized by addition of histidine-tagged proteins and, optionally, antibodies. The resulting fiber assemblies are useful in applications such as antigen capture, immunoanalysis and multiplexed analysis.

BACKGROUND OF THE INVENTION

Polymer-based fibers are attractive platforms to perform functions in a variety of field applications. (Kumbar, S. G., et al., *J Nanosci and Nanotech* 2006, 6, (9-10), 2591-2607; Woolfson, D. N., et al., *Curr Opin in Chem Biol* 2006, 10, (6), 559567; Steinbacher, J. L., et al., *J Polymer Sci* 2006, 44, (22), 6505-6533; Ji, F. L., et al., *Smart Materials & Structures* 2006, 15, (6), 1547-1554; Pavon-Djavid, G., et al., *Biomacromolec* 2007, 8, (11), 3317-3325.) Standard methods are available for the hierarchical assembly of individual fibers into controllable patterns, e.g. fabrics. As hair-like materials, fibers can be spun into filaments, thread or rope, which can then be woven into fabrics. Fibers can also be flattened into sheets, as in creation of paper or felt.

Standard methods for the assembly of fibers into controllable patterns may be used to assemble individual fibers of varying lengths, generating one-dimensional yarns and ropes, two-dimensional fabrics, and even three-dimensional structures (Pavlov, M. P., et al., *Macromolec Biosci* 2004, 4, (8), 776-784; Ding, B., et al., *Nanotechnol* 2006, 17, (15), 3685-3691.). Such patterns are useful as scaffolds, substrates, templates, platforms and the like for the assembly of other polymer and inorganic materials. With or without other materials, the patterns are useful in a variety of applications including various analysis, detection, separation and/or purification methods.

Fibers may be derived from natural materials or may be entirely man-made. The materials utilized for fibers vary widely and the choice of material for fibers depends on the intended use of the fibers. Various characteristics of the fibers may be characteristics natural to the fiber material or the fibers may be "functionalized" to possess a desired characteristic.

Figure 1:
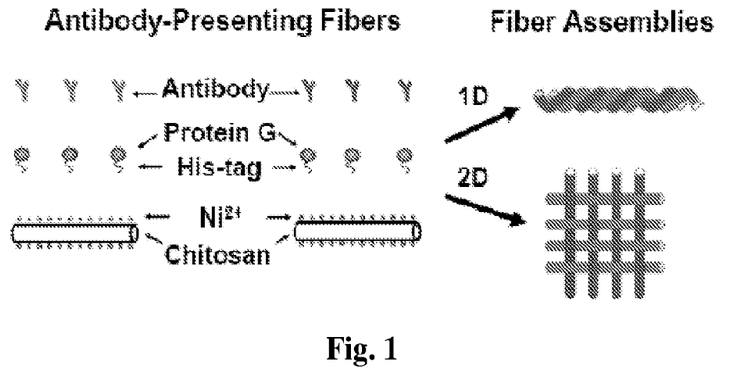
FIG. 1 is an illustration of the antibody-presenting fiber assemblies of the invention.
Figure 2:
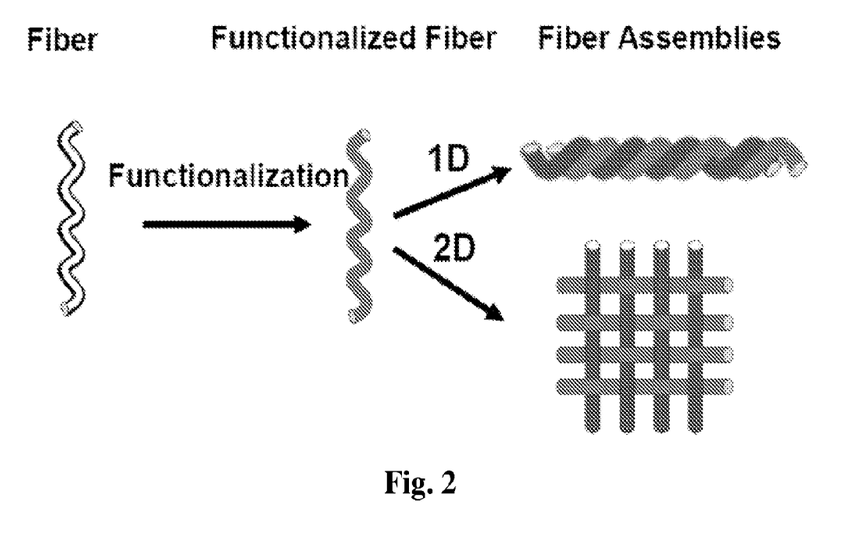
FIG. 2 is an illustration of a general scheme to functionalize individual fibers or fiber assemblies to extend their capabilities.

Functionalization of fibers can be utilized to impart various characteristics upon fibers. The most familiar type of functionalization is dying to impart color to a fiber—then, different colored fibers can be woven to generate fabrics with a nearly infinite combination of colors and patterns. FIG. 2 provides a general scheme of functionalization of individual fibers or fiber assemblies to extend their capabilities. Current development and/or use of functionalized fibers relates to properties such as stain resistance (Hegemann, D., *Adv Engin Mat* 2005, 7, (5), 401-404.), antimicrobial properties (Lim, S. H., et al., *J Macromolec Sci* 2003, C43, (2), 223-269; Duran, N., et al., *J Biomed Nanotech* 2007, 3, (2), 203208; Bang, E. S., et al., *J Appl Polymer Sci* 2007, 106, (2), 938-943.), catalytic activities (Xu, L., et al., *J Catalysis* 2000, 195, (2), 394-405.), electronic capabilities (Marculescu, D., et al., Electronic textiles: A platform for pervasive computing. *Proceedings of the IEEE* 2003, 91, (12), 1995-2018.), odor resistance, UV resistance, resistance to absorption of oil or water, and resistance to static electricity, as well as many other such properties.

Chitosan is a natural, linear polyaminosaccharide derived from the shells of crustaceans such as crabs, lobster, shrimp, and the like. It is also found in many insects (especially those with exoskeletons), various mushrooms and fungi. It has a chemical structure similar to that of cellulose. Chitosan is known to be biodegradable, biocompatible, bioabsorbable and non-toxic with a strong antibacterial effect. It is utilized in fibers used in a variety of textiles, and has use in medical, health, pharmacological, and industrial applications.

There remains a need in the art for fibers that are functionalized to impart distinct biological activities to the individual fibers for use in analytical processes, such as immunoanalysis, multiplexed analysis and other analyses involving antigen capture. The present invention satisfies this need and provides additional advantages.

SUMMARY OF THE INVENTION

The present invention relates to the production and use of biofunctionalized fibers and protein assembly systems containing such fibers.

Thus, in one aspect the invention provides a biofunctional fiber comprising a fiber platform and a histidine-tagged protein. In another aspect the invention provides protein fiber assemblies containing such biofunctional fibers.

In a further aspect, the invention provides a method of making an antibody-presenting fiber assembly, comprising 1) providing a fiber platform; 2) reacting the fiber platform with a His-tagged protein selected from among protein G, protein G3T, His-GFP, and His-RFP, to generate a protein-tagged fiber; 3) incubating the protein-tagged fiber with an antibody-containing solution to generate an antibody-presenting fiber; and 4) assembling one or more antibody-presenting fibers into a one-dimensional, two-dimensional, or three-dimensional antibody-presenting fiber assembly.

In a still further aspect, the invention provides a method of capturing an antigen, comprising incubating an antibody-presenting fiber assembly comprising a fiber platform and an antibody linked to the fiber platform, with an antigen-containing medium, wherein the antibody linked to the fiber platform binds the antigen in the antigen-containing medium.

The invention also provides a method of immunoanalysis, comprising incubating an antibody-presenting fiber assembly comprising a fiber platform and an antibody linked to the fiber platform, with a sample, wherein binding of the antibody linked to the fiber platform to an antigen in the sample is indicative of the presence of the antigen in the sample.

In another aspect, the invention provides a method of multiplexed analysis, comprising incubating an antibody-presenting fiber assembly comprising two or more antibody-presenting fibers, each fiber comprising an antibody linked to a fiber platform, with a sample, wherein each antibody linked to a fiber platform binds its respective antigen in the sample.

In an additional aspect, the invention provides a method of protein recovery, comprising 1) providing a biofunctionalized fiber comprising a nickel-chitosan fiber; 2) incubating the biofunctionalized fiber with a histidine-tagged protein-containing sample to generate a protein-tagged fiber; and 3) recovering the protein tagged fiber from the sample.

BRIEF DESCRIPTION OF THE DRAWINGS

FIG. 6(a) shows fluorescence imaging and image analysis of the fiber of Example 4 and FIG. 6 (b) is a graph of the antigen binding as a function of fiber length.

FIG. 9(a) Optical and fluorescence images showing His-GFP binding to chitosan fibers. Fibers are wrapped around a glass tube—the upper fiber was contacted with $Ni^{2+}$ prior to incubation with His-GFP while the lower fiber is a control that was not contacted with $Ni^{2+}$. FIG. 9(b) Confocal image of $Ni^{2+}$-chitosan fiber with assembled His-GFP. FIG. 9(c) SEM image of $Ni^{2+}$-chitosan fiber with assembled His-GFP.

FIG. 10(a) analyzes the robustness of the binding. FIG. 10(b) shows analysis of the reversibility of the binding.

FIG. 13(b) Image analysis of fiber segments; FIG. 13(c) Relationship between fiber fluorescence and antibody concentration in initial solution; FIG. 13(d) Antibody assembly per cm of fiber length determined after solubilizing antibody-presenting fiber segments; and FIG. 13(e) Confocal image showing antibody assembly in outer 50 μm shell of the fiber segment.

FIG. 14(a) Fluorescence photomicrographs of fiber segments incubated with varying amounts of antigen (GFP); FIG. 14(b) Image analysis of fiber segments; FIG. 14(c) Relationship between fiber fluorescence and antigen concentration; FIG. 14(d) Antigen binding per cm of fiber length determined after solubilizing antigen bound fiber segments; FIG. 14(e) Confocal image showing antigen (GFP) binding in outer 25 μm shell of the fiber segment.

FIG. 15(a) Antibody-presenting fibers for anti-GFP and anti-RFP were wrapped around a glass tube, immersed in a solution containing both antigens and imaged using both green and red filters (left image), or a single filter for green (upper right image) or red (lower right image); FIG. 15(b) Antibody-presenting fibers for anti-GFP and antistreptavidin were "woven" into a mesh, immersed in a solution containing both antigens (streptavidin was fluorescently labeled) and imaged using both green and red filters.

DETAILED DESCRIPTION OF THE INVENTION

The present application provides biofunctionalized fibers and protein fiber assemblies comprising biofunctionalized fibers. The invention also provides methods of making and methods of using such protein assemblies in applications such as antigen capture, immunoanalysis and multiplexed analysis. In a specific embodiment, the present invention provides biofunctionalized fibers made up of chitosan fibers and His-tagged proteins and, optionally, antibodies.

Fibers are a versatile platform for protein fiber assemblies of the present application because standard methods are available for the hierarchical assembly of individual fibers into controllable patterns (e.g., fabrics). As used herein, the term "fiber" or "fibers" refers to a fundamental unit of a protein assembly structure of the invention. A fiber is generally characterized as having a length dimension which is much greater than its diameter or width. Any length of fiber may be used in the invention. Fibers of the invention encompass filaments, strips, ribbons and any other form of fiber. Fragments of longer fibers are also encompassed within the term "fiber."

Fibers utilized in the protein fiber assemblies of the invention may be generated by any method known to those of skill in the art. Such methods may include, but are not limited to extrusion, spinning and electrospinning. An exemplary method of preparation of chitosan fibers is provided in Example 1 below. In another embodiment the fibers are extruded. Extruded fibers can have virtually any cross-sectional shape, including, but not limited to: round, elliptical, and ribbon shaped. Various other methods for preparing fibers are known and are encompassed by this application.

Fibers of the present invention may compose any material known as a stable platform for the desired function. However, in one embodiment the invention provides chitosan-containing fibers. Chitosan-containing fibers possess desirable characteristics such as biodegradability, biocompatibility, bioabsorbability, non-toxicity and a strong antibacterial effect. Chitosan's pH-responsive, network-forming properties allow fibers to be spun or electrospun (Schiffman, J. D., et al., *Biomacromol* 2007, 8, (2), 594-601.), and this capability provides the opportunity to generate antibody presenting fibers, as described more fully hereinafter.

By the present application, biofunctionalization of individual fibers by the reversible binding of proteins is provided. The invention further provides generation of a protein assembly structure using such biofunctionalized fibers in simple multi-fiber structures.

In one embodiment, the invention provides biofunctional fibers. A preferred fiber platform is aminopolysaccharide chitosan. Chitosan is a versatile biopolymer that offers both fiber-forming and metal-binding properties (Payne, G. F., et al., *Soft Matter* 2007, 3, (5), 521-527; Rinaudo, M., Chitin and chitosan: Properties and applications. Progress in *Polymer Science* 2006, 31, (7), 603-632; Yi, H. M., et al., *Biomacromol* 2005, 6, (6), 2881-2894; Wei, Y. C., et al., *J Polymer Sci* 1992, 30, (10), 2187-2193; Rathke, T. D., et al., *J Macromol Sci* 1994, C34, (3), 375-437; Nair, L. S., et al., *Expert Opinion on Biological Therapy* 2004, 4, (5), 659-668; El-Tahlawy, K., et al., *J App Polymer Sci* 2006, 100, (2), 1162-1168; Schiffman, J. D., et al., *Biomacromol* 2007, 8, (2), 594-601; Schiffman, J. D., et al., *Biomacromol* 2007, 8, (9), 2665-2667; Muzzarelli, R. A. A., *Natural chelating polymers: alginic acid, chitin and chitosan*. New York: Pergamon Press: 1973; Rhazi, M., et al., *Euro Polymer J* 2002, 38, (8), 1523-1530; Schauer, C. L., et al., *Thin Solid Films* 2003, 434, (1-2), 250-257; Guibal, E., Interactions of metal ions with chitosan-based sorbents: a review. *Separation and Purification Technology* 2004, 38, (1), 43-74; Shi, Q. H., et al., *Biochem Eng J* 2003, 16, (3), 317-322; Xi, F. N., et al., *J Chromatog* 2004, 1057, (1-2), 41-47; Gamage, A., et al., *Food Chemistry* 2007, 104, (3), 989-996; Qin, Y. M., et al., *J Appl Polymer Sci* 2007, 105, (2), 527-532.). Compared to other polymers, chitosan is unique because this aminopolysaccharide can form fibers and can participate in simple protein assembly mechanisms (e.g., nickel-mediated assembly).

In one embodiment the fiber is functionalized by addition of a histidine-tagged protein to the fiber platform. Exemplary histidine-tagged proteins useful in methods of the invention include, but are not limited to, His-protein G, His-GFP, His-RFP and modifications thereof, including His-protein G3T, a modified protein G.

Biofunctionalization of the fiber by attachment of a histidine-tagged protein may include a direct reaction between the fiber platform and the protein, or the reaction may be mediated. Protein G is a streptococcal IgG-binding protein that selectively binds and orients antibodies to present their antigen-binding sites (Akerstrom, B., et al., *J Immunol* 1985, 135, (4), 2589-92; Rusmini, F., et al., *Biomacromol* 2007, 8, (6), 1775-89; Vijayendran, R. A., et al., *Anal Chem* 2001, 73, (3), 471-80; 5. Lee, J. M., et al., *Anal Chem* 2007, 79, (7), 2680-2687). Example 3 below presents direct binding of a His-tagged streptococcal antibody-binding protein (modified protein G, termed G3T) to the fiber platform.

Figure 3:
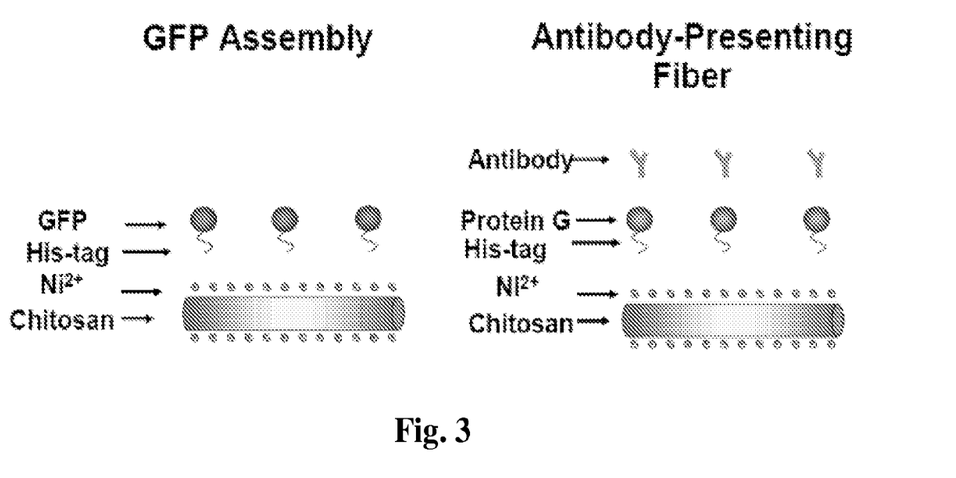
FIG. 3 is an illustration of a general scheme of the invention in generation of GFP linked to a chitosan fiber platform generation of antibody-presenting fibers of the invention.
Figure 9:
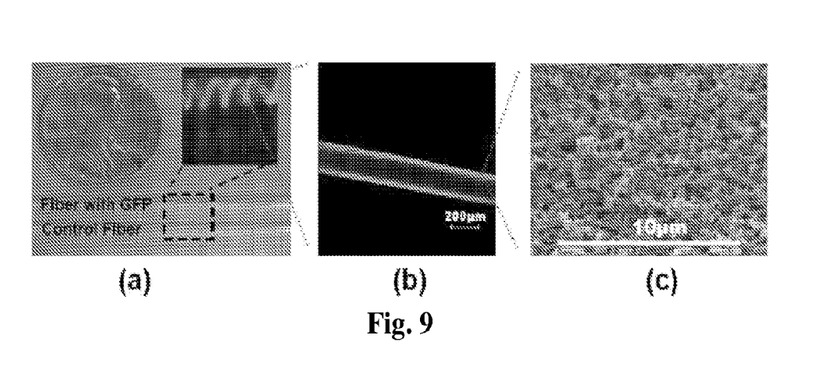
FIG. 9 is a series of photographs demonstrating nickel mediated His-GFP binding to chitosan fiber, as described in Examples 9 and 10.

Previous studies have indicated that nickel can mediate binding between chitosan membranes and His-tagged proteins (Ahmed, S. R., et al., *J Memb Sci* 2006, 280, (1-2), 553-559). Therefore, in one embodiment nickel is utilized to mediate the reversible binding of histidine-tagged proteins (Blankespoor, R., et al., *Langmuir* 2005, 21, (8), 3362-3375; Cresce, A. V., et al., *Macromolecules* 2006, 39, (17), 5826-5829; Kim, S. H., et al., *J Am Chem Soc* 2007, 129, (43), 13254-13264; Lata, S., et al., *Anal Chem* 2005, 77, (4), 1096-1105; Paborsky, L. R., et al., *Anal Biochem* 1996, 234, (1), 60-65; Tinazli, A., et al., *Na Nanotech* 2007, 2, (4), 220225; Zhen, G. L., et al., *Adv Funct Mater* 2006, 16, (2), 243-251; Jain, P., et al., *Biomacromol* 2007, 8, (10), 3102-3107) to the fiber, as illustrated in FIGS. 3 and 9 and Examples 6 and 9 below, and mentioned in Example 2 utilizing the models His-GFP and His-G3T.

In one embodiment of the invention, a nickel-containing fiber without a protein attached may be utilized to probe for histidine-tagged proteins in a sample, e.g., cell lysates. As such, this method is useful in applications where immobilized metal affinity chromatography might presently be used. An exemplary use of this method is provided in Example 13.

A biofunctionalized fiber of the invention may further comprise an antibody. Examples 3, 7 and 14 demonstrate the assembly of antibodies onto biofunctionalized fibers to generate antibody-presenting fibers. Antibody assembly onto the fiber was shown to be controllable, and antigen-binding to these antibody-presenting fibers was measured (Examples 4, 8, and 16). Importantly, antibody and antigen were observed to penetrate substantially into the individual fibers (tens of microns) to allow the assembly of picomole (pmole) levels of protein per cm of fiber length.

In one embodiment, a biofunctionalized fiber of the invention comprises chitosan, at least one histidine-tagged protein, and at least one antibody.

Detection of binding of biofunctionalized fibers, whether between the functionalized fiber and the histidine-tagged protein, or between the antibody-presenting fiber and an antigen, may be detected by methods known to those of skill in the art, including, but not limited to, detection of fluorescence, utilizing fluorescence tags such as GFP, RFP, FITC, Texas red, and the like.

Fibers of the invention may be used in formation of one, two or three dimensional protein assembly structures. Such protein assembly structures may be assembled by weaving, knitting, braiding, twisting, bundling, stacking, layering, meshing, wrapping, or any other known method of assembling individual fibers.

Protein assembly structures of the invention may be single fiber, dual fiber or multifiber structures, in that they can variously comprise: 1) one type of fiber with a single functionality, 2) one type of fiber with multiple functionalities, 3) more than one type of fiber, each with a single functionality, 4) more than one type of fiber, each with multiple functionalities, or 5) more than one type of fiber, with a mixture of functionalities. Therefore, the protein assembly structures of the invention may have a single functionality or may have multiple functionalities.

As demonstrated in FIG. 2 and in Examples 5, 8 and 17, antibody-presenting fibers with different specificities were assembled into simple 1D and 2D structures, and individual fibers in these fiber assemblies were observed to capture their respective antigens from antigen mixtures. In one embodiment, the present invention provides assembly of two His-tagged proteins, the model green fluorescence protein (GFP) and an engineered version of the streptococcal antibody-binding protein, protein G. (Tanaka, G., et al., *Anal Biochem* 2006, 350, (2), 298-303.)

In another specific embodiment, the invention provides protein assembly structures made up of biofunctionalized fibers, where the functionalization provided to the fibers provides specificity to a particular antigen, due to the presence of one or more antibodies in the fiber or fibers within the protein assembly structures. As mentioned, the protein assembly structures of the invention may have a single specificity or may have multiple specificities.

Protein assembly structures of the invention are useful in a variety of applications, dependent on the functionalization of the fibers in the protein assembly structure.

In one embodiment, the invention provides a method of antigen capture where protein assembly structures of the invention are utilized to capture antigens within a sample medium specific to the antibodies present on the biofunctionalized fibers.

In another embodiment, the invention provides a method of immunoanalysis in which protein assembly structures of the invention are utilized in the analysis of a sample, wherein the sample potentially contains one or more antigens within a sample medium specific to the one or more antibodies present on the biofunctionalized fibers. The occurrence of binding shows that that the antigens are present in the sample medium.

Additionally, the invention provides a method of multiplexed analysis in which protein assembly structures of the invention are utilized in the analysis of a sample, wherein the sample potentially contains more than one antigen within a sample medium specific to two or more antibodies present on the biofunctionalized fibers. The occurrence of binding shows that the antigens are present in the sample medium. This method of analysis is unique in that the protein assembly structures are made up of more than one type of fiber, and the fibers are combined in any fashion described above, generating a one, two or three dimensional structure. Each fiber included in a protein assembly structure utilized in multiplexed analysis may have a single specificity or may have multiple specificities. Examples of such analysis are provided below in Examples 5, 8 and 17. Multiplexed analysis has utility in analysis of samples, e.g. environmental samples.

Additional applications of the protein fiber assemblies of the invention include use as a convenient means to enlist biological activities (e.g., recognition and catalysis) in field applications. For instance, protein fiber assemblies may be useful in single-use, multiplexed, point-of-care diagnostics. Additionally, biofunctionalized fibers of the invention may be woven into fibers into clothing to provide detection and protection capabilities.

In one embodiment, the present invention provides reversible, nickel-mediated assembly of proteins to fibers of the aminopolysaccharide chitosan. Protein assembly to fibers is important because proteins confer specific biological functionalities, and because fibers can be further assembled from the bottom-up into hierarchical structures with multiplexed and patterned functionalities. Such assembly is demonstrated in the Examples below. Specifically, generation of antibody-presenting fibers is provided in Examples 3, 7 and 14, assembly of fibers with two different specificities into simple 1D and 2D structures is provided in Examples 5, 8, and 17, and demonstration of the ability of individual fibers in these fiber assemblies to capture their respective antigens from mixtures is demonstrated in Examples 4, 8 and 16.

The following examples are intended to illustrate, but not limit, the invention.

In the examples, the following materials and methods were utilized:

The following materials were purchased from Sigma-Aldrich; Tween 20, chitosan from crab shells (85% deacetylation), phosphate-buffered saline (PBS; 0.01M, pH=7.4), and imidazole. Luria Broth (LB) medium was purchased from Becton Dickinson. Non-fat dry milk was purchased from BioRad. Nickel chloride hexahydrate was purchased from EM Science (Cherry Hill, N.Y.). BugBuster protein extraction reagent was purchased from Novagen (Madison, Wis.).

The two His-tagged proteins (His-GFP and His-protein G) were prepared by fermentation as described below. The GFP antigen was prepared by cleavage of the His tag from fermentation-derived His-GFP as described below. Two additional antigens were tested; Red Fluorescence Protein (RFP) was purchased from Biovision (Mountain View, Calif.), and streptavidin (labeled with Alexa Fluor 594) was purchased from Invitrogen (Eugene, Oreg.). Four antibodies were used in this study; Anti-Red Fluorescent Protein (anti-RFP) from rabbit and anti-Green Fluorescent Protein (anti-GFP) from goat were purchased from Rockland (Gilbertsville, Pa.), anti-mouse antibody from goat that was labeled with Alexa Fluor 488 was purchased from Invitrogen (Eugene, Oreg.), and anti-streptavidin from rabbit was purchased from Sigma.

Histidine-tagged green fluorescent protein (His-GFP) was expressed from *E. coli* BL21 containing pTrcHisGFPuv plasmid. His-GFP was purified from cell lysates using immobilized metal affinity chromatography (IMAC) as described previously. (Cha, H. J., et al., *Biotech and Bioeng* 2000, 67, (5), 565-574.) In some cases, the His tag was cleaved using enterokinase and the GFP without a His-tag was purified by IMAC. Protein G is a streptococcal IgG-binding protein. (Akerstrom, B., et al., *J Biol Chem* 1986, 261, (22), 240-247; Akerstrom, B., et al., *J Immun* 1985, 135, (4), 2589-2592.) In this example, an engineered version of protein G was utilized that had been constructed to have 3 repeats of the streptococcal protein G Fc-binding domain (Tanaka, G., et al., *Anal Biochem* 2006, 350, (2), 298-303), and an N-terminal histidine tag, and a short tyrosine-rich sequence at the C-terminus, were added. Details of the cloning and expression are provided below.

Protein recovery from cell lysates was analyzed by using SDS-PAGE. The protein was analyzed by denaturing at 95° C. for 10 minutes and then run on a 12.5% SDS-PAGE at 150 volts for 1 hour. The gel was then stained by Coomassie blue for two hours and destained with acetic acid buffer. The picture of the gel was taken by an AlphaImager system.

Fiber fluorescence was observed with a Leica fluorescence microscope (MZFL III) using an excitation filter at 480/40 nm and emission barrier filter at 510 for anti-mouse antibody, excitation 425/60 nm and emission 480 nm for GFP, excitation 560/55 nm and emission 645 nm for RFP and streptavidin. Fluorescence photomicrographs were taken using a digital camera (spot 32, Diagnostic Instrument) connected to the fluorescence microscope. The fluorescence profiles of the micrographs were analyzed using Image J software (http://rsb.info.nih.gov/ij/). In some cases, the fluorescence of the wet fibers was observed using a Zeiss LSM 510 scanning confocal microscope with an Ar laser at 488 nm. Quantitative analysis of antibody-assembly and antigen binding to the chitosan fibers was measured by first dissolving segments of the fibers in 300 µl acetic acid buffer (0.1M, pH=5.0) in 96-well plates, and then measuring the fluorescence using a Luminescence spectrometer (PerkinElmer LS 55).

The surface morphology of a chitosan fiber with bound GFP was observed using an Amray 1820D scanning electron microscope (SEM) operated at 20 kV. Prior to analysis, the fiber was dried by $CO_2$ critical point drying and sputtered with gold palladium (AuPd) using Denton DV 502 vacuum evaporator.

Example 1

Preparation of Chitosan Fibers

Figure 4:
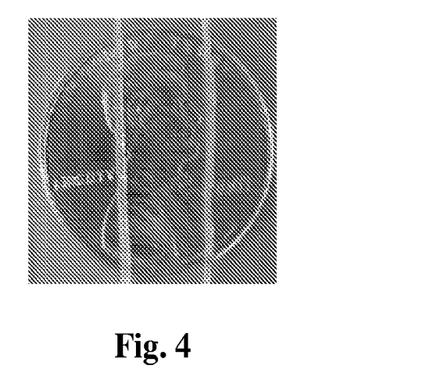
FIG. 4 is an optical micrograph that provides a perspective of the fiber size (~500 μm diameter in this case).

Chitosan fibers were prepared by injecting a chitosan (Sigma, St. Louis, Mo.) solution (1.6 w/v %, pH=5.0) through a 27 gauge needle into an aqueous solution containing 20% ethanol and 1 M NaOH, and allowing the fibers to incubate in this bath for 10 minutes. FIG. 4 shows an optical image of two fibers (in this case the fiber diameter was approximately 500 µm).

Example 2

Preparation of a Chitosan-Protein G Complexed Fiber

A protein G fusion with elastin was obtained by the Bentley group from the Kobatake group in Japan. The protein G contained three repeats of the antibody-binding domain and 72 repeats of the pentapeptide derived from the hydrophobic domain of elastin (designated E72G3). (Tanaka, G., et al., *Anal Biochem* 2006, 350, (2), 298-303; Gao, D. et al., *J Am Chem Soc* 2006, 128, (3), 676-7.) The elastin sequences allow the E72G3 protein to adhere non-covalently to hydrophobic surfaces. To promote protein G assembly to chitosan fibers, E72G3 was modified by deleting the elastin repeats and adding a pentatyrosine sequence to the C-terminus to generate G3T. The tyrosine tag of the G3T protein can be enzymatically activated by the enzyme tyrosinase for covalent conjugation to chitosan (U.S. Pat. No. 7,288,532). Alternatively, the G3T can be bound to chitosan fibers through a hexahistidine tag using nickel chelation (chitosan binds nickel and can mediate assembly of G3T via its his-tag).

The chitosan fibers were rinsed with PBS, and the G3T protein was assembled by contacting the fibers overnight with a solution of G3T (0.8 µM) and tyrosinase (100 U/ml), and then incubating the fibers for 15 minutes with $NaBH_4$ (0.2% w/v in PBS). After enzymatic assembly of G3T, the fibers were blocked (5% nonfat milk in PBS).

Example 3

Preparation of Antibody-Presenting Chitosan Fiber Assembly Using Protein G

Figure 5:
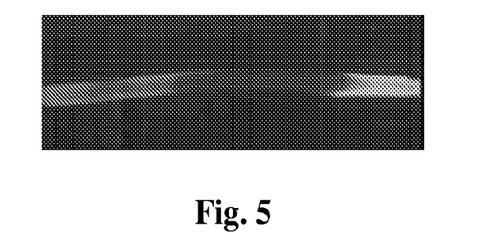
FIG. 5 is a fluorescence image showing the versatility of antibody assembly onto chitosan fibers by demonstrating the assembly of two different fluorescently-labeled antibodies at different ends of a fiber as described in Example 3.

An initial study was performed to assemble two antibodies at separate locations on a single fiber. This was achieved by simultaneously immersing each end of the fiber generated in Example 2 into separate antibody solutions; a goat anti-rabbit antibody labeled with Texas red (0.1 µM) and a goat anti-mouse antibody labeled with FITC (0.1 µM). The fluorescence image in FIG. 5 shows assembly of the labeled antibodies at separate "addresses" on the fiber, while no fluorescence is observed in the middle of the fiber where no antibody was assembled.

Example 4

Antigen Binding by Antibody-Presenting Chitosan Fiber Assembly

The antigen binding ability of the antibody-presenting chitosan fibers prepared above was examined. The fibers were sequentially incubated with tyrosinase plus G3T, anti-GFP antibody, and the GFP antigen. The fluorescence photographs and associated image analysis indicates considerable binding of the GFP antigen to the fiber on the right of FIG. 6*a*. In contrast, the control fiber on the left (tyrosinase was deleted during the G3T assembly step) shows little fluorescence and therefore little binding of the GFP antigen. Thus, antibody-presenting chitosan fibers can be readily generated for antigen capture.

To estimate the extent of antigen binding to the fibers, individual fibers were dissolved using mild acid (0.1 M acetate buffer, pH 5.0) and the fluorescence in solution was measured.

Figure 6:
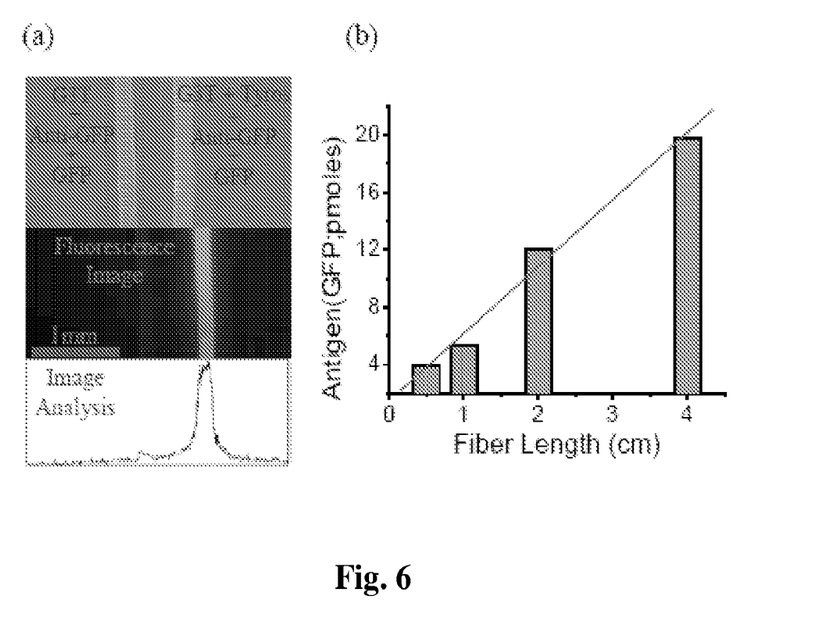
FIG. 6 shows the results of antigen binding to antibody-presenting chitosan fibers as described in Example 4.

The slope of the graph of antigen binding as a function of fiber length in FIG. 6*b* indicates that 5 pmole of the GFP antigen is bound per cm of the antibody-presenting chitosan fiber. If the cross-sectional area of GFP is estimated to be 8 $nm^2$/molecule, then a "fractional" surface coverage of antigen on the fiber is on the order of 2. This estimate suggests that antigen-antibody binding is not confined to the external surface of the chitosan fiber but that some binding occurs within the fiber network.

Figure 7:
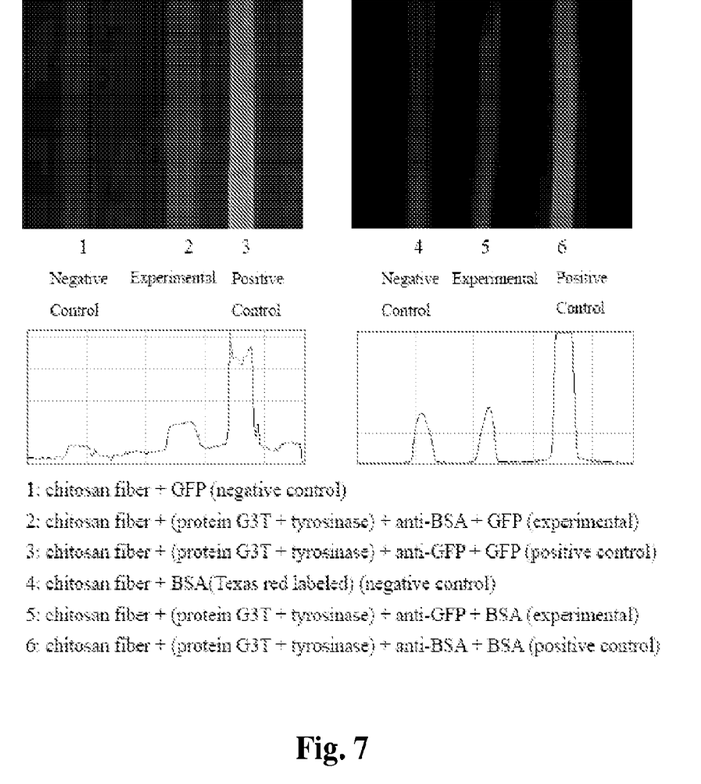
FIG. 7 shows fluorescence photographs and graphs illustrating specificity of antigen binding to various antibody-presenting chitosan fibers as set forth in Example 4.

Using the same method, chitosan fibers were prepared to present either anti-GFP antibody or anti-BSA antibody. The selectivity of these fibers was examined for antigen capture by incubating them either with GFP (0.17 µM) or labeled-BSA (0.08 µM, Texas-red labeled). The first three fibers in FIG. 7 were incubated with GFP. The negative control shows little non-specific binding of GFP to chitosan (Fiber 1). Fiber 2 shows little GFP binding to the chitosan fiber presenting the anti-BSA antibody. Fiber 3 is the positive control and shows substantial binding of the GFP antigen to the anti-GFP presenting chitosan fiber. The last three fibers in FIG. 7 were incubated with the fluorescently-labeled BSA. The results with Fiber 4 show some non-specific binding of BSA to chitosan, while BSA-binding to the anti-GFP presenting Fiber 5 is similar to this background binding. As expected, substantial BSA binding was observed for the chitosan fiber presenting the anti-BSA antibody (Fiber 6). These results indicate that the antibody-presenting chitosan fibers can selectively capture their antigens although the selectivity could be improved by reducing non-specific binding.

Example 5

Simultaneous Multiple Antibody Capture

Figure 8:
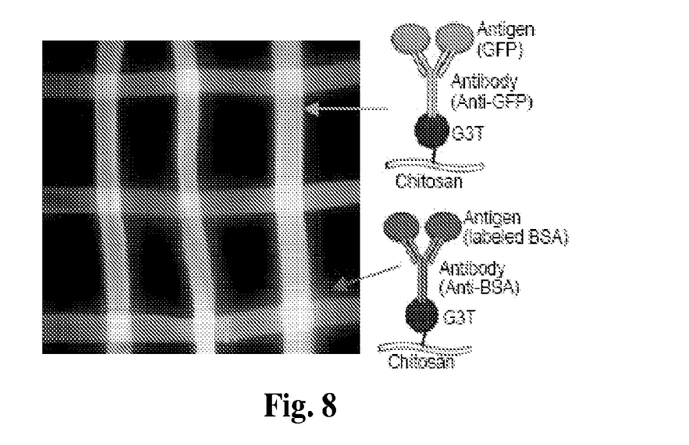
FIG. 8 shows a fluorescence photograph and graphic representation of a mesh woven as described in Example 5. The mesh is woven from anti-GFP presenting fibers (vertical) and anti-BSA presenting fibers (horizontal) and provides for capture of multiple antigens.

A loose fiber mesh was created from both the anti-GFP presenting and the anti-BSA presenting fibers, and this mesh was incubated for 1 hour with an antigen mixture containing GFP (0.17 µM) and Texas-red-labeled BSA (0.08 µM). This mesh was then immersed in a solution containing a mixture of both the GFP and BSA antigens (BSA was fluorescently labeled for imaging). FIG. 8 shows fluorescence images for this mesh and indicates that each antigen is assembled on its respective fiber. These results indicate that woven fabrics can be prepared to capture multiple antigens simultaneously.

Example 6

Preparation of a Chitosan Complexed Fibers Using Nickel

An additional fiber assembly was generated as detailed in Example 2 above, with the use of nickel to mediate the binding between the his-tag on G3T and chitosan.

The chitosan fibers were incubated with nickel solution (0.01M $NiCl_2$ in 0.9% NaCl, pH=5.0) for 1 hour at room temperature. The resulting fiber was washed with PBS buffer 3 times. The $Ni^{2+}$-chitosan fibers were then blocked in 5% nonfat milk in PBS for 2 h. The resulting nickel-chitosan fibers were incubated with one of the following proteins: 1) G3T solution for 1 hour and G3T binds to chitosan fiber via the coordination of Ni and His-tag on G3T; 2) His-GFP; or 3) His-protein G. As described in the text, some protein assembly experiments were performed using crude cell lysates, and other experiments were performed using solutions of purified protein.

Example 7

Preparation of Antibody-Presenting Chitosan Fiber Assembly Using Protein G

To generate antibody-presenting fibers, $Ni^{2+}$-chitosan fibers were first prepared, blocking the fibers with 5% nonfat milk, and assembling protein G by incubation with a solution of His-tagged protein G (1.4 µM for 1 hour). After washing with PBS 3 times, the fiber was incubated with antibody-containing solutions (the types and concentrations of antibody varied as described in the Results and Discussion), and then washed with Tween-containing PBS (0.1% Tween). Antigen-binding was studied by incubating the antibody-presenting fibers with antigen for 1 hour.

Example 8

Antigen Binding by Antibody-Presenting Chitosan Fiber Assembly

To demonstrate the concept of multi-functional fiber assemblies, antibody-presenting fibers specific for GFP, RFP, and streptavidin were prepared, and two of these fibers were assembled into either a 1D or 2D assembly. These fiber assemblies were challenged by immersion in solutions containing both antigens.

Example 9

Preparation of a Chitosan-GFP Complexed Fiber Using Nickel

The model green fluorescent protein that had an N-terminal hexahistidine-tag (His-GFP) was assembled to $Ni^{2+}$-chitosan fibers. GFP was assembled by incubating the $Ni^{2+}$-chitosan fiber with His-GFP solution (0.3 µM) and incubating for 1 h. The control chitosan fiber was not contacted with nickel prior to incubation with the His-GFP solution. These two fibers were wrapped onto separate glass tubes, and FIG. 9a shows that these fibers are transparent to white, and mechanically flexible. The fluorescence photomicrograph in FIG. 9a shows strong GFP fluorescence for the upper $Ni^{2+}$-chitosan fiber while little fluorescence is observed for the control chitosan fiber that was not treated with $Ni^{2+}$. This initial experiment indicates that nickel can mediate the selective assembly of proteins to chitosan fibers.

Example 10

Confocal Analysis of a $Ni^{2+}$-Chitosan Fiber with Bound GFP

The $Ni^{2+}$-chitosan fiber with bound GFP was further examined using confocal laser scanning fluorescence microscopy. The image in FIG. 9b indicates that His-GFP is assembled uniformly along the fiber length and that this protein assembles within an outer shell region of the fiber. The thickness of this outer shell was estimated to be approximately 30 µm, which indicates that His-GFP can penetrate substantially into the fiber. The surface of this fiber was further examined using scanning electron microscopy (SEM). The SEM image in FIG. 9c shows that the fiber surface is coarse, and the observed porosity may provide access for protein diffusion. The ability of GFP to assemble deeply within an individual chitosan fiber suggests that nickel-mediated binding allows fibers to be funtionalized with considerable amounts of protein.

Example 11

Robustness of Nickel-Mediated Binding of Chitosan and Protein

Figure 10:
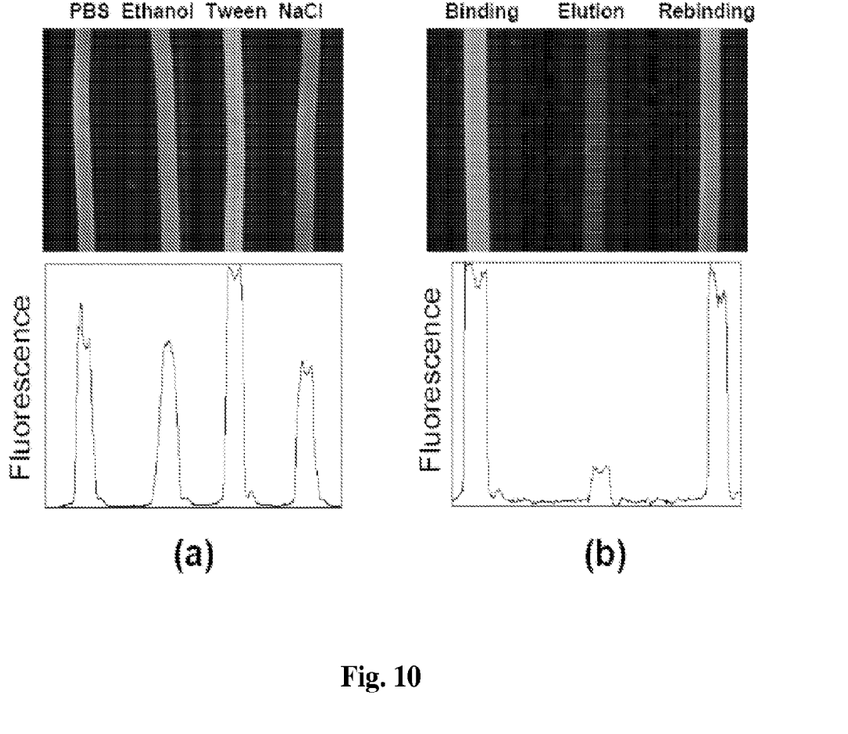
FIG. 10 is a fluorescence photograph and graphic analysis of nickel-mediated protein-chitosan binding, as analyzed in Examples 11 and 12.

The robustness of nickel-mediated binding was next examined. After assembling His-GFP (0.6 µM) to a $Ni^{2+}$-chitosan fiber, the fiber was cut into four equal segments. Individual fiber segments were incubated for 1 hour in solutions of; PBS buffer, a mixture of PBS plus 30% ethanol, a mixture of PBS plus 1% Tween 20, or an aqueous solution with 1M NaCl. After incubation, the fiber segments were rinsed and imaged using a fluorescence microscope, and the fluorescence intensity was estimated using standard image analysis software. FIG. 10a shows each fiber segment has similar fluorescence, which suggests that that the majority of the His-GFP remains bound to the $Ni^{2+}$-chitosan fiber segments under the conditions investigated (note: no effort was made to discern whether changes in fluorescence were due to GFP unbinding or denaturation, or fiber shrinkage). These results indicate that nickel-mediated protein assembly to the $Ni^{2+}$-chitosan fiber is reasonably robust.

Example 12

Reversability of Nickel-Mediated Binding of Chitosan and Protein

To ensure Ni-mediated binding is reversible, a $Ni^{2+}$-chitosan fiber with bound His-GFP was immersed in an "elution" buffer (0.25 M imidazole, pH=8) for 10 min. As shown in FIG. 10b, the majority of the GFP fluorescence (≈85%) was removed by this short treatment with the elution buffer. After elution, the $Ni^{2+}$-chitosan fiber was re-incubated with His-GFP (0.6 µM) to allow for re-binding. FIG. 10b indicates that re-binding resulted in 95% of GFP fluorescence compared to the initial fiber. These results indicate that nickel-mediated protein binding to chitosan fibers can be reversed by treatment with imidazole, and that imidazole treatment does not prevent subsequent protein binding.

Example 13

Recoverability of Histidine-Tagged Proteins by Functionalized Fibers

Figure 11:
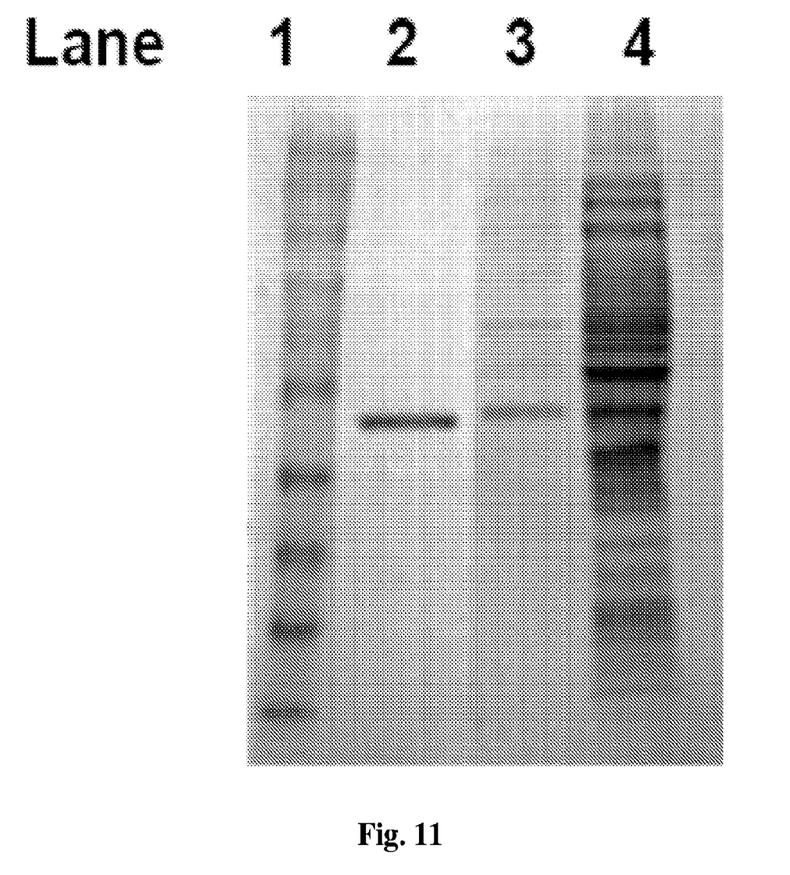
FIG. 11 provides photographs of SDS-gels run in analysis of the ability of biofunctionalized fibers to bind histidine-tagged proteins as described in Example 13.

Since the predominant use of nickel-mediated protein binding is for protein recovery by immobilized metal affinity chromatography, the $Ni^{2+}$-chitosan fibers were tested for the recovery of His-GFP from cell lysates. Specifically, His-GFP-expressing E. coli cells were lysed, the lysate was centrifuged, and the supernatant was contacted with a $Ni^{2+}$-chitosan fiber for 20 minutes (1 ml supernatant contacted with a 40 cm long fiber). After washing the fiber with PBS and 0.01 M imidazole, His-GFP was eluted using imidazole (0.25 M, pH=8) for 10 min and analyzed using SDS-PAGE. FIG. 11 shows gels stained with Coomassie blue. The protein eluted from the $Ni^{2+}$-chitosan fiber is shown in Lane 3 and this can be compared to the purified His-GFP standard (Lane 2) and the crude cell extract (Lane 4). Lane 1 provides a molecular weight standard. This comparison indicates that binding and elution to the $Ni^{2+}$-chitosan fiber can be used to recover His-tagged proteins from cell extracts, although optimization studies will be required to improve purity. These results suggest that chitosan fibers can provide an alternative material for the nickel-mediated recovery of His-tagged proteins.

Example 14

Preparation of Antibody-Presenting Chitosan Fiber Assembly Using Protein G

Figure 12:
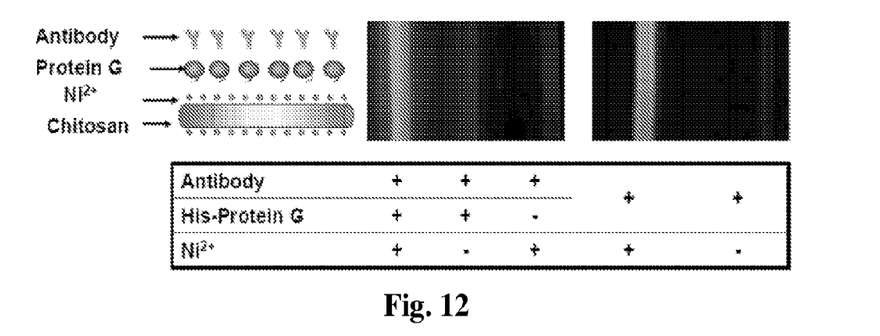
FIG. 12 provides an analysis of nickel mediated antibody assembly to chitosan fibers through a His-tagged protein G as described in Example 14. The photograph on the left is of the fiber resulting from reaction of a $Ni^{2+}$-chitosan fiber and His-tagged protein G, then with fluorescently-labeled antibody. The photograph on the right is of the fiber resulting from reaction of protein G complexed with fluorescently labeled antibody and then contacted with the $Ni^{2+}$-chitosan fiber.

In the next phase of the study, the nickel-mediated assembly of antibodies to chitosan fibers as illustrated in FIG. 2 was examined. Initially, two slightly different assembly sequences were examined. In the first sequence, $Ni^{2+}$-chitosan fibers were incubated for 1 hour with a solution containing the His-tagged protein G (2 ml of 0.8 µM for 1 hour), and then the protein G-functionalized chitosan fibers were incubated with antibodies. To visualize antibody assembly a fluorescently-labeled antibody (anti-mouse antibody labeled with Alex fluor 488; 2 ml of 0.2 µM for 1 hour) was used. The fluorescence photomicrograph at the left in FIG. 12 shows strong fluorescence, which indicates that antibody is bound to this protein G-chitosan fiber assembly. The controls for this experiment were fibers prepared without treatment with nickel or the His-tagged protein G, and the images in the left-most fluorescence photomicrograph indicate little antibody assembly to these control fibers. These results indicate that nickel-mediated protein G binding to chitosan enables the subsequent assembly of antibodies to the fibers.

In the second antibody assembly sequence, His-tagged protein G (0.8 µM) was contacted with antibody (0.3 µM) to allow protein G to complex with the antibody, and then this complex was contacted with the $Ni^{2+}$-chitosan fiber. Again, the fluorescently-labeled anti-mouse antibody was used for visualization and a control fiber was prepared without nickel treatment. The fluorescence photomicrograph at the right in FIG. 12 shows significant fluorescence in the experimental fiber, with limited fluorescence in the control. This result suggests that nickel can mediate the assembly of a pre-formed protein G-antibody complex to the chitosan fiber through protein G's His tag.

Example 15

Figure 13:
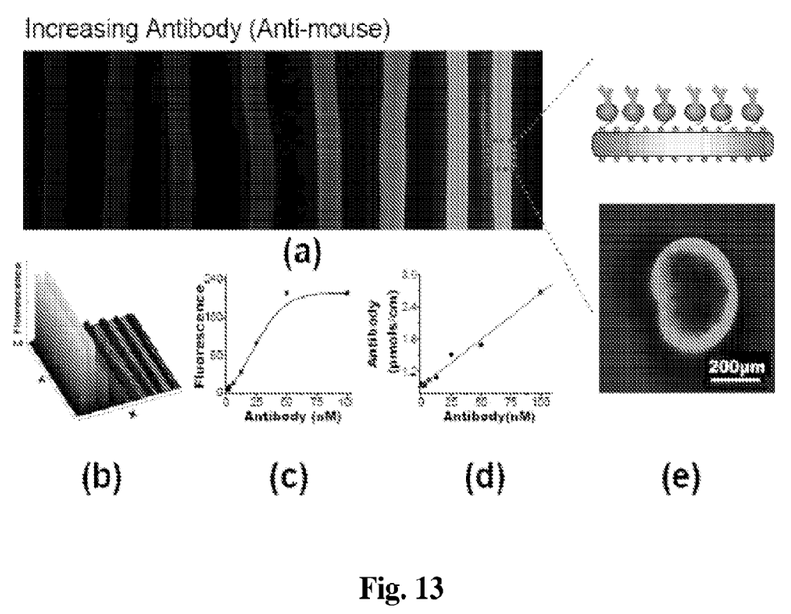
FIG. 13 provides the results of controlled antibody assembly to fibers, as described in Example 15 where FIG. 13(a) Fluorescence photomicrographs of fiber segments incubated with varying amounts of antibody.

Control and Analysis of Antibody Attachment to Biofunctionalized Chitosan Fibers To examine whether antibody assembly to the fiber can be controlled, protein G-modified chitosan fiber segments were contacted with varying amounts of antibody. Specifically, $Ni^{2+}$-chitosan fiber segments (2 cm length and 500 µm diameter) were functionalized by incubation for 1 hour with His-tagged protein G (1.4 µM in 2 ml). After rinsing, the protein G-functionalized fiber segments were incubated for 1 hr with fluorescently-labeled anti-mouse antibody (0.78-100 nM in 0.5 ml), and the resulting antibody-presenting fibers were rinsed and imaged using a fluorescence microscope. As expected, FIG. 13a shows increased fluorescence for fiber segments incubated with higher concentrations of labeled antibody. The fluorescence intensities of these fiber segments were estimated from the images as shown in FIG. 13b. As expected, the fiber's average fluorescence intensity is observed in FIG. 13c to increase with the concentration of antibody in the solution. This result indicates that antibody-presenting fibers can be prepared with controllable levels of antibody.

To provide an order-of-magnitude estimate of the amount of antibody assembled on the fiber, chitosan's pH-dependent solubility was exploited. In this case, the 2 cm segments of the antibody-presenting fibers were dissolved in acetate buffer (0.1 M, 2 ml, pH 5), the fluorescence of the resulting solution was measured, and this fluorescence was compared to a standard curve generated for fluorescently-labeled antibody. FIG. 13d shows that pmole amounts of antibody are assembled per cm of fiber.

To assess the radial distribution of antibody, confocal microscopy was used to examine a fiber segment prepared from a 100 nM antibody solution. The cross-section shown in FIG. 13e indicates that the fluorescently-labeled antibody is bound to the outer 50 µm shell of the fiber segment. Assuming the antibody ($\approx$2 pmol per cm fiber length) is confined to this outer volume ($\approx 7 \times 10^8$ µm$^3$/cm), then the antibody concentration in this shell can be estimated to be 3 µM, which is a 30-fold concentration increase compared to the initial antibody-containing solution.

Example 16

Antigen Binding by Antibody-Presenting Chitosan Fibers

Figure 14:
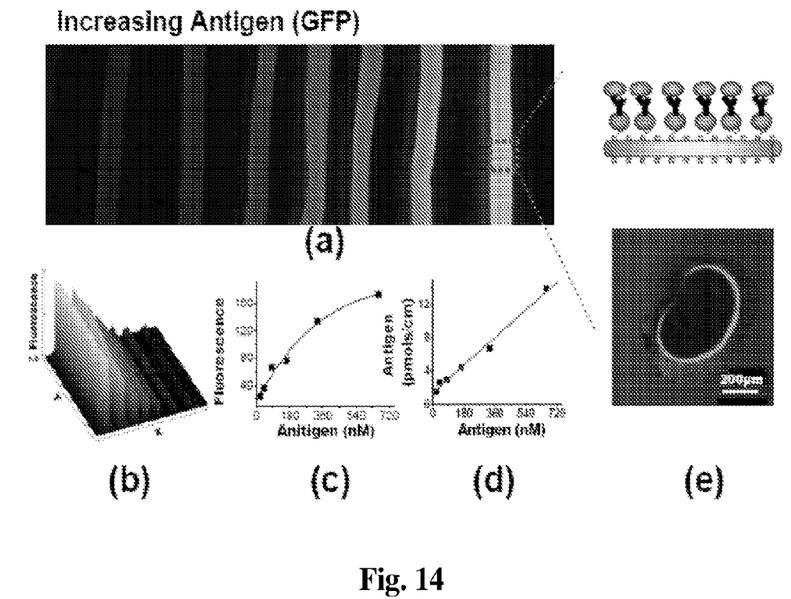
FIG. 14 provides the results of antigen binding to antibody-presenting fiber segments, as described in Example 16.

Next, the ability of the antibody-presenting fibers to bind antigen was examined. For this study, anti-GFP-presenting fibers were prepared by assembling His-tagged protein G onto the $Ni^{2+}$-chitosan fiber segment, and then allowing the anti-GFP antibody (2 ml of 0.3 µM for 1 hour) to bind. These anti-GFP presenting fiber segments were then immersed in solutions containing varying concentrations of the GFP antigen (21-660 nM in 0.5 ml). [Note: the GFP antigen used in this study lacked the His tag.] As expected, FIG. 14a-c shows that anti-GFP-presenting fibers incubated with higher GFP levels have higher fluorescence. From the analysis of solubilized fiber segments, FIG. 14d shows that pmole levels of the GFP antigen are bound to the anti-GFP-presenting fibers. Finally, the confocal image in FIG. 14e suggests that antigen binding to the fiber incubated with 660 nM antigen is confined to the outer 25 µm shell of the fiber. Using the same calculation as described above, it is estimated that the antigen concentration in the outer shell of the fiber is 17 µM, which represents a nearly 30-fold increase in concentration compared to the antigen concentration in the initial solution.

Example 17

Preparation of Multiplexed Fiber Assemblies

In the final studies, the potential for combining fibers of differing functionalities into hierarchical assemblies was demonstrated. In one study, two antibody-presenting fibers were prepared and assembled into a 1D structure. The individual fibers were prepared by assembling His-tagged protein G onto the $Ni^{2+}$-chitosan fiber segment, and then assembling antibody by contacting the segment with solutions of either anti-GFP antibody (2 ml of 0.2 µM for 1 hour) or anti-RFP antibody (2 ml of 0.2 µM for 1 hour). These two fibers were then wrapped onto a glass tube. The ability of these individual fibers to capture their antigens was evaluated by immersing the tube into a solution (2 ml) containing both the GFP (0.1 µM) and RFP (0.1 µM) antigens. After rinsing, the fibers were imaged using a fluorescence microscope. The image at the left of FIG. 15a was prepared using both green and red filters, and this image indicates the individual antigens were captured by individual fibers of this "assembly". When a single filter was used for imaging, the images to the right of FIG. 15a further indicate that individual antigens were selectively captured by their respective fibers with little non-specific binding.

Figure 15:
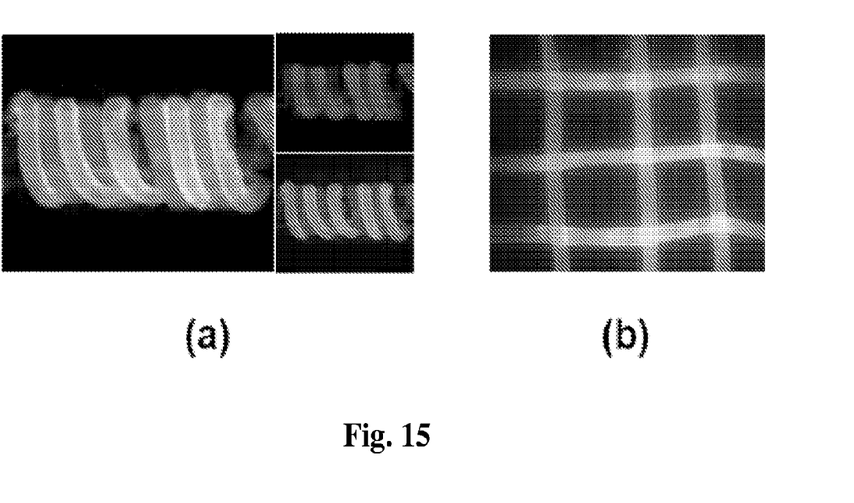
FIG. 15 provides the results of antigen recognition by separately-functionalized fibers assembled into 1D and 2D structures, as described in Example 17.

A second fiber assembly was generated by preparing two antibody-presenting fibers and loosely assembling them into a 2D mesh. In this case, the anti-GFP presenting fiber was generated as described above, and an anti-streptavidin fiber was prepared by contacting a protein G-functionalized fiber with a solution containing anti-streptavidin antibody (2 ml of 0.2 µM for 1 hour). The ability of the individual fibers to capture their antibodies was tested by immersing the mesh in a solution (2 ml) containing a mixture of both the GFP (0.1 µM) and labeled-streptavidin (0.1 µM Alexa Fluor 594 labeled streptavidin) antigens. The image in FIG. 15b shows GFP is captured by the anti-GFP fibers (shown horizontally) while the labeled streptavidin is captured by the anti-streptavidin fibers (shown vertically). The results in FIG. 15 demonstrate the potential for combining antigen-presenting fibers through standard methods (e.g., spinning and weaving) to create multifunctional and patterned assemblies.

Although the invention has been described with reference to the above examples, it will be understood that modifications and variations are encompassed within the spirit and scope of the invention, as hereinafter claimed.

What is claimed is:

1. A biofunctional fiber comprising a fiber platform comprising chitosan or chitosan-containing fibers and a hexahistidine-tagged tagged protein.

2. The biofunctional fiber of claim 1, wherein the fiber platform comprises chitosan.

3. The biofunctional fiber of claim 1, wherein the hexahistidine-tagged protein is an IgG-binding protein.

4. The biofunctional fiber of claim 1, further comprising nickel.

5. The biofunctional fiber of claim 1, further comprising an antibody.

6. A protein fiber assembly comprising one or more biofunctional fibers, wherein the biofunctional fiber comprises a fiber platform comprising chitosan or chitosan-containing fibers and a hexahistidine-tagged tagged protein.

7. The protein fiber assembly of claim 6, wherein the fiber platform comprises chitosan.

8. The protein fiber assembly of claim 6, wherein the hexahistidine-tagged protein is an IgG-binding protein.

9. The protein fiber assembly of claim 6, wherein the biofunctional fiber further comprises nickel.

10. The protein fiber assembly of claim 6, wherein the biofunctional fiber further comprises an antibody.

11. The protein fiber assembly of claim 10, wherein the assembly comprises two or more fibers and the fibers comprise the same antibodies.

12. The protein fiber assembly of claim 10, wherein the assembly comprises two or more fibers and the fibers comprise different antibodies.

13. The protein fiber assembly of claim 6, wherein the fiber assembly is one-dimensional, two-dimensional, or three-dimensional.

14. The protein fiber assembly of claim 6, wherein the fiber assembly comprises yarn, rope or fabric.

15. A method of antigen capture, immunoanalysis, or multiplexed analysis comprising contacting the fiber assembly of claim 6 with a sample medium for antigen capture, immunoanalysis, or multiplexed analysis.

16. A method of making an antibody-presenting fiber assembly comprising:
    providing a fiber platform comprising chitosan or chitosan-containing fibers;
    reacting the fiber platform with a hexahistidine-tagged IgG-binding protein;
    incubating the protein-tagged fiber with an antibody-containing solution, to generate an antibody-presenting fiber; and
    assembling one or more antibody-presenting fibers into a one-dimensional, two-dimensional, or three-dimensional antibody-presenting fiber assembly.

17. The method of claim 16, wherein the fiber platform comprises chitosan.

18. The method of claim 16, further comprising reacting the fiber platform with nickel prior to reacting the fiber platform with the hexahistidine-tagged protein.

19. The method of claim 16, wherein the antibody-presenting fiber assembly comprises two or more antibody-presenting fibers and the fibers comprise different antibodies.

* * * * *

UNITED STATES PATENT AND TRADEMARK OFFICE
CERTIFICATE OF CORRECTION

| | | |
|---|---|---|
| PATENT NO. | : 8,791,239 B2 | Page 1 of 1 |
| APPLICATION NO. | : 12/990981 | |
| DATED | : July 29, 2014 | |
| INVENTOR(S) | : Xiao-Wen Shi | |

It is certified that error appears in the above-identified patent and that said Letters Patent is hereby corrected as shown below:

Title Page, Item 87: "PCT Pub. Date: Nov. 22, 2009" should be -- PCT Pub. Date: Nov. 12, 2009 --.

In the Claims

Claim 1, Column 15, lines 43-44: "and a hexahistidine-tagged tagged protein" should be -- and a hexahistidine-tagged protein --.

Signed and Sealed this
Fourth Day of November, 2014

Michelle K. Lee
*Deputy Director of the United States Patent and Trademark Office*